United States Patent [19]

Blumenthal et al.

[11] Patent Number: 5,556,556
[45] Date of Patent: Sep. 17, 1996

[54] METHOD FOR PRODUCING ENDOTHERMIC ATMOSPHERES AND NON-CATALYTIC PROBE THEREFOR

[76] Inventors: Robert N. Blumenthal, 17470 Bard Ct., Brookfield, Wis. 53005; Andreas T. Melville, 204 N. 86th St., Milwaukee, Wis. 53226

[21] Appl. No.: 359,869

[22] Filed: Dec. 20, 1994

Related U.S. Application Data

[60] Continuation of Ser. No. 212,370, Mar. 11, 1994, abandoned, which is a division of Ser. No. 800,607, Nov. 27, 1991, Pat. No. 5,324,415, which is a continuation of Ser. No. 364,024, Jun. 9, 1989, abandoned.

[51] Int. Cl.$^6$ .................................................. G01N 27/409
[52] U.S. Cl. ...................... 205/784.5; 204/409; 204/424; 204/427; 204/428
[58] Field of Search ................ 204/183.18, 421–429; 205/783.5, 784, 784.5, 785

[56] References Cited

U.S. PATENT DOCUMENTS

| | | | |
|---|---|---|---|
| Re. 28,792 | 4/1976 | Ruka et al. | 204/153.18 |
| 3,011,873 | 12/1961 | Davis, II | 436/149 |
| 3,058,815 | 10/1962 | Davis, II | 422/93 |
| 3,177,563 | 4/1965 | Pennell | 29/159.2 |
| 3,259,527 | 7/1966 | Beggs | 148/16.5 |
| 3,442,773 | 8/1969 | Wilson | 204/427 |
| 3,598,381 | 8/1971 | Schwalm et al. | 266/5 |
| 3,606,285 | 9/1971 | Bayer | 263/34 |
| 3,662,996 | 5/1972 | Schwalm et al. | 266/4 A |
| 3,773,641 | 11/1973 | Fitterer | 204/153.18 |
| 3,843,419 | 10/1974 | Schmidt et al. | 148/16.5 |
| 3,913,988 | 10/1975 | Scales et al. | 308/8.2 |
| 4,012,709 | 3/1977 | Logothetis et al. | 73/23 |
| 4,071,817 | 1/1978 | Bahl | 204/153.18 |
| 4,093,195 | 6/1978 | Schwalm | 266/251 |
| 4,158,166 | 6/1979 | Isenberg | 204/153.18 |
| 4,162,889 | 7/1979 | Shigemura | 431/76 |
| 4,166,610 | 9/1979 | Yamazaki et al. | 266/89 |
| 4,183,213 | 1/1980 | Rao | 60/517 |
| 4,198,279 | 4/1980 | Brown et al. | 204/408 |
| 4,230,651 | 10/1980 | Rao | 264/29.7 |
| 4,284,487 | 8/1981 | Barnes et al. | 204/428 |
| 4,290,586 | 9/1981 | Kane et al. | 266/80 |
| 4,313,799 | 2/1982 | Perkins | 204/153.18 |
| 4,351,182 | 9/1982 | Schmidberger | 73/27 R |
| 4,362,580 | 12/1982 | Kane et al. | 148/16 |
| 4,436,289 | 3/1984 | Connelly et al. | 266/80 |
| 4,462,872 | 11/1982 | Nelson | 204/428 |
| 4,588,493 | 5/1986 | Blumenthal et al. | 204/428 |
| 4,591,132 | 5/1986 | Wunning | 266/80 |
| 4,597,807 | 7/1986 | Fenstermaker et al. | 148/16.5 |
| 4,606,807 | 8/1986 | Mendenhall | 204/433 |
| 4,752,361 | 6/1988 | Gautschi | 204/424 |
| 4,754,952 | 7/1988 | Hattori et al. | 266/80 |
| 4,763,880 | 8/1988 | Smith et al. | 266/87 |
| 4,966,348 | 6/1989 | Schneider | 266/79 |
| 5,324,415 | 6/1989 | Blumenthal et al. | 204/427 |

OTHER PUBLICATIONS

Metals Handbook, Ninth Edition, vol. 4, Heat Treating, American Society for Metals, 1981 pp. 422–424, 428–429.
"Carbon/Oxygen Sensors/Process Controllers/Data Acquisition/Automated Atmosphere Control Systems", *AACC*, Zircoa Inc. 1989.
"A Thermodynamic Study on Carburizing of Plain Carbon and Alloy Steels", Jong–Il Hwang, BS/MS, Dissertation Submitted to the Marquette University Graduate School in Partial Fulfillment of the Requirement for the Degree of Doctor of Philosophy, Milwaukee, Wisconsin Jul. 1986.
Photos (View 1, 2, 3) Prior Art Sample Tube.

*Primary Examiner*—T. Tung
*Attorney, Agent, or Firm*—Ryan, Maki, Mann & Hohenfeldt

[57] ABSTRACT

Disclosed herein is a gas sampling system for analyzing the oxygen partial pressure in a gas carburizing atmosphere. The system is appropriate for remote sensing of gas when the probe can't be fitted in the heat treating apparatus. Sooting of the sampled gas tube and probe is eliminated by use of ceramic, non-catalytic surfaces in the measuring vessel. A ceramic feed pipe, with a small diameter, introduces the gas to be measured into the vessel and increases the velocity of the gas to avoid sooting.

10 Claims, 1 Drawing Sheet

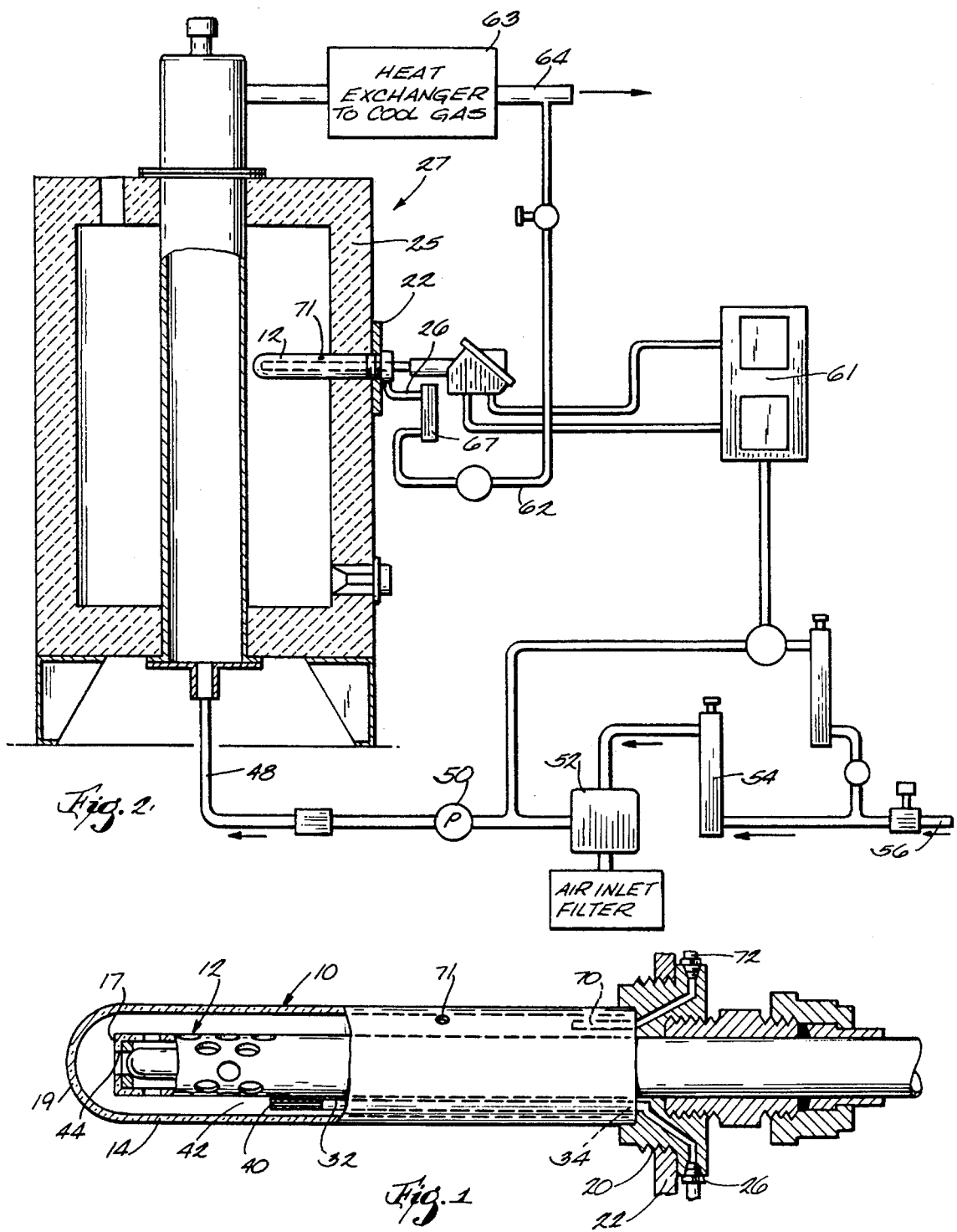

METHOD FOR PRODUCING ENDOTHERMIC ATMOSPHERES AND NON-CATALYTIC PROBE THEREFOR

CROSS REFERENCE TO RELATED APPLICATION

This is a continuation of application Ser. No. 08/212,370, filed on Mar. 11, 1994, now abandoned, which is a divisional of application Ser. No. 07/800,607, filed Nov. 27, 1991, now U.S. Pat. No. 5,324,415, which is a continuation of Ser. No. 07/364,024, filed Jun. 9, 1989 (Abandoned).

FIELD OF THE INVENTION

This invention relates to apparatus and methods for producing endothermic atmospheres and to non-catalytic probes for analyzing such atmospheres.

BACKGROUND OF THE INVENTION

Background on patent application for a gas sampling system utilizing a remote ceramic gas tube assembly and ceramic oxygen probe combination to be used for analyzing the oxygen partial pressure, $Po_2$, in a gas carburizing atmosphere.

Oxygen probes utilizing a solid electrolyte have been used to control the carbon potential in carburizing atmosphere for the last fifteen years. The oxygen probes are typically installed directly into the furnace atmosphere (i.e. an in situ type installation). A discussion of carbon potential control in carburizing is described in Control of Surface Carbon Content, *Metals Handbook*, Vol. 4, pp. 417–431, 9th Edition, 1981. When an in situ type oxygen probe is used to measure the oxygen content in an atmosphere used for carburizing or neutral hardening, the general guideline is that the probe should be exposed to the same gas atmosphere and temperature as the work is exposed to. A frequent problem in some installations is that the length of the probe is too short to meet the above general guidelines for an in situ type probe installation. For example, in most rotary retort type carburizing furnaces, the length of a typical commercial oxygen probe used for controlling the carburizing process is not long enough to reach that part of the furnace which has the same atmosphere and temperature that the parts being carburized are exposed to. Another example of this problem is an endothermic generator where natural gas and air are reacted at an elevated temperature (e.g. 1900° F.) in the presence of a nickel catalyst to produce an endothermic atmosphere. For a description of endothermic generators, see for example: *Metals Handbook*, Vol 4, pp. 389–416, 9th Edition, 1981. The use of an in situ type oxygen probe in some commercial endothermic generators is not feasible because either the length of the probe is insufficient or because of the difficulties and cost associated with this type of installation.

An alternative to the in situ type oxygen probe analysis is to use an oxygen probe in conjunction with a gas sampling technique. The Davis U.S. Pat. Nos. 3,058,815 and 3,011,873 show the use of a separate furnace to maintain a gas measuring sensor at a temperature comparable to that of the gas in the heat treating furnace.

The following is a brief discussion of problems that arise when an oxygen probe is used in conjunction with a gas sampling technique to analyze a gas atmosphere removed from either an endothermic generator or a carburizing furnace. The composition of a typical carrier or carburizing atmosphere is described in *Metals Handbook*, Vol. 4, pp. 417–431, 9th Edition, 1981. When an endothermic or carburizing atmosphere is cooled by removing it from a heated chamber, the following reactions take place:

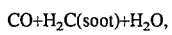

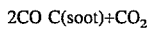

The reason that the carburizing atmosphere tends to produce carbon in the form of soot as the temperature is lowered is that the equilibrium constant for both of the above reactions increases with decreasing temperature.

Thus, cooling of an atmosphere with a carbon potential will favor the formation of carbon (soot) and increase the concentration of $H_2O$ and $CO_2$ in the gas sampled atmosphere. The amount of $H_2O$, $CO_2$ and carbon (soot) formed by the above reactions will depend on the kinetics (i.e. these reactions are time and temperature dependent). If catalytic surfaces are present, the rate at which these reactions proceed will be increased. It should be noted that according to thermodynamic considerations the formation of carbon (soot) and the equilibrium partial pressure of $H_2O$ and $CO_2$ increase as the temperature decreases. The rate of these reactions, however, will decrease as the temperature is decreased according to kinetic theory. Thus, there is a temperature range where the formation of carbon (soot) and increased concentration of $H_2O$ and $CO_2$ will be favored (i.e. approximately 900° F.–1500° F.). The lower temperature limit is determined primarily by kinetic considerations. Whereas, the upper temperature limit is determined by both thermodynamic and kinetic considerations and the composition of the carburizing atmosphere. For example, if an atmosphere with a high carbon potential is used, the upper temperature limit where sooting may begin is increased and if a gas with a low carbon potential is used the upper temperature limit is decreased. Similar problems are encountered when the sampled gas is reheated in the sampled gas tube assembly. During reheating, the temperature of the carrier or carburizing gas increases until the temperature is the same as the endothermic generator or furnace in which it is placed. During the time that the temperature of the gas is reheating, between approximately 900° F.–1500° F., sooting will tend to occur as described in the aforementioned reactions. In the current state of the art, the gas is reheated in a heat-resistant, stainless steel alloy tube. A problem in practice is that the metal alloy tube fills up with soot which either blocks the flow of gas or effects the accuracy of the oxygen probe analysis. The soot then has to be removed by physically taking the sampled gas tube apart and cleaning it. The frequency of cleaning the metal alloy tube may be as often as every few days which is very undesirable. One of the problems with the current state of the art is that the metal alloy tube used to reheat the carburizing atmosphere catalyzes the above sooting reactions. Because of the sooting reaction the composition of the atmosphere is altered. For example, both the $CO_2$ and $H_2O$ content is increased. Thus, the voltage output of the oxygen probe is also altered resulting in an inaccurate gas analysis.

SUMMARY OF THE INVENTION

The principal object of this invention is to provide a gas sampling system utilizing a ceramic or ceramic coated metal sampled gas tube assembly and an oxygen probe combination to provide a relatively maintenance-free system which gives an accurate and representative analysis of an appropriately sampled carburizing atmosphere. This invention does not directly address the problems associated with removal of a gas sample from an endogenerator or a furnace. The problem is less severe in the case of an endogenerator because the gas is rapidly cooled in either a water or air cooled heat exchanger to minimize the aforementioned sooting reactions.

In accordance with this invention, the problem of sooting and the associated alteration of the composition of a gas sample during reheating is minimized or eliminated by the combination of a non-catalytic ceramic remote gas tube, a small diameter ceramic gas inlet tube, and an oxygen probe comprised primarily of ceramic components. By replacing the metal alloy sample gas tube with a ceramic tube, the catalytic surfaces are eliminated and the rate of the aforementioned reactions are significantly reduced. The utilization of a small diameter ceramic gas inlet tube greatly increases the linear flow rate of the gas introduced into the sampled gas tube. The result of the high linear flow rate is to reduce the amount of time that the gas is in the critical temperature range (i.e. approximately 900° F.–1500° F.) where the aforementioned undesirable reactions take place. Thus as a result of the significantly reduced time in the critical temperature range, and the use of a non-catalytic ceramic material such as alumina or mullite, the amount of the Undesirable reaction that takes place is essentially eliminated. The temperature of the gas exiting the ceramic inlet tube should be above the highest critical temperature for sooting. After exiting the inlet tube, the gas flows into the sampled gas tube. The linear flow rate decreases significantly, because the ID of the gas sampled gas tube is much larger than the ID of the inlet tube. The lower linear flow rate is important because more time is made available for the water gas reaction to equilibrate. To obtain accurate analysis of the gas using an oxygen probe, it is important that the water gas reaction:

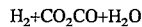

$$H_2 + CO_2 \rightleftharpoons CO + H_2O$$

be in thermodynamic equilibrium.

A discussion of the importance of equilibrium of the water gas reaction in control of carbon potential using an oxygen probe is described in Control of Surface Carbon Content, *Metals Handbook*, Vol. 4, pp. 417–431, 9th Edition 1981. Although oxygen probes with different basic designs could be used with the above sampled gas tube, we prefer the use of an oxygen probe with a ceramic sheath as described in U.S. Pat. No. 4,588,493 the entire disclosure of which is incorporated herein by reference. The use of ceramic components minimize the catalytic surfaces that would favor the formation of carbon (soot) in accordance with the above reaction. Since the end of the oxygen probe (i.e. the region within 4 to 5 inches of the end of the probe) should be exposed to temperature near or above the critical temperature where sooting occurs, thus, the use of non-catalytic ceramic materials is not so critical.

Further objects, advantages and features of the invention will become apparent from the following disclosure.

DETAILED DESCRIPTION OF THE DRAWINGS

FIG. 1 is a fragmentary sectional view of the sampled gas measuring vessel with an oxygen sensor probe.

FIG. 2 is a schematic diagram of a control system with an endogenerator employing the sampled gas vessel.

DESCRIPTION OF A PREFERRED EMBODIMENT

FIG. 1 is a sectional view of the sampled gas measuring vessel of the invention which includes an outer chamber or vessel 10 in which the gas measurements take place. A ceramic probe 12 is provided having an outer ceramic sheath 14 made in accordance with FIG. 4 of my U.S. Pat. No. 4,588,493, the entire disclosure of which is incorporated herein by reference. This probe is selected because of its non-catalytic effect on the gases, which are being tested to minimize the problem of creating soot in the vessel 10. Supporting means are provided for supporting said vessel. In the disclosed construction the supporting means includes a threaded end 20 on the vessel 10 which can be anchored in a mounting plate 22 which in turn can be fastened to an outer wall 25 of the endogenerator 27 (FIG. 2). This arrangement will keep the gas at an appropriate temperature corresponding to the temperature of the carburizing atmosphere in the endogenerator for accurate measurement. Thus, the endogenerator which contains the endothermic atmosphere which is being measured is used to maintain the probe 12 at the same temperature range as the gas being measured, although the gas to be measured is withdrawn from the endogenerator.

The vessel 10 is also provided with means for connecting the vessel 10 to the furnace gas. In the disclosed construction the means includes fitting 26 which is connectable to a source of the carburizing gas as hereinafter described.

In accordance with the invention, The vessel is also provided with an inlet tube or feed pipe 32 which has an inlet 34 in communication with the inlet passage 26. The outlet end 40 of the inlet tube is located in the passage 42 and proximate the end 19 of the vessel. The end 40 is also adjacent the inlet 44 of the measuring probe to deliver the gases to be measured into the probe. The feed pipe 32 has a small diameter (0.089" I.D.) selected to move the gas quickly to the inlet 44 of the probe to minimize the catalytic contact time of the gas on any surfaces prior to exposure to the measuring elements in the probe. The system includes a flow meter 67 with a valve to change the flow rate. The desired volume flow rate is 1 to 10 ft.³/hr. and the desired linear flow rate will range from 300 ft./min. to 4000 ft./min. The preferred linear flow rate is 1500 ft./min. The vessel outer wall is provided with a outlet 71 which controls the pressure internally of the vessel and provides a balance to the flow rate through the feed pipe 32. An outlet 71 having a diameter of 0.1" or 2.5 mm has been successfully tested with a feed tube having this diameter. A positive pressure is maintained in the vessel interior to prevent backflow of atmospheric gas into the vessel through opening 71. The flow drops adjacent the inlet 44 down to 4 feet per minute because of the large cross-section of the area inside of the vessel when a 1.75 inch ID is employed. The desired linear flow rate is 1 to 10 ft./min. and the preferred linear flow rate is 4 ft./min. As an alternative to the aperture 71, an exhaust tube 70 is provided with a fitting 72. The tube 70 is used when discharge of the measured gases into the atmosphere or furnace is not appropriate.

The gas to be reacted in the endothermic generator, air and natural gas, is delivered to the furnace 27 by a circuit which includes a conduit 48, pump 50 and other conventional apparatus including a mixing carburetor 52, meter 54, reaction gas inlet and a control panel 61 which regulates the flow of gas and gas mixture in accordance with the sensed data provided by the probe 12. The endothermic atmosphere is withdrawn from the generator by gas pipe 64. The end 17 of the probe 12 is desirably about one inch from the end 19 of the vessel. The end 40 of the feed pipe 32 is desirably about four inches from the end 19. Such an arrangement has provided good results. These dimensions were employed in subsequently described tests.

In tests conducted using the above measuring system we have found agreement between the dew point calculated from the emf of the oxygen probe and the appropriate thermodynamic data and measured dew point of the gas sampled from an endothermic generator. For example, the relationship between the dew point, D.P., in °C. as a function of temperature, T, in °K. and oxygen probe output, E, in millivolts and hydrogen content, $H_2$, in %. These results may be represented by the following equation:

$$D.P. (°C.) = \left[ \frac{5422.18}{14.3983 - \frac{28,664.5}{T(°K.)} + 2.2558 \log T(°K.) - 2.3026 \log \frac{\% H_2}{100} + \frac{23.215 E(mv)}{T(°K.)}} \right] - 273.16$$

We claim:

1. A method for producing within a reaction chamber a treatment atmosphere having a carbon potential and subject to formation of carbon when exposed to a prescribed sooting temperature condition, the method comprising the steps of:

heating the reaction chamber to a desired temperature condition above the prescribed sooting temperature condition, reacting a mixture of gases to produce a treatment atmosphere at the desired temperature condition within the heated reaction chamber, locating an external sensor within a sample tube outside the reaction chamber for analyzing an atmosphere sample, the sample tube having an interior that extends along an axis and has a distal end, the external sensor being located within the sample tube interior near the distal end, heating at least the distal end of the sample tube interior to the desired temperature condition, withdrawing a sample of the treatment atmosphere from the reaction chamber through a gas pipe while cooling the sample from the desired temperature condition within the gas pipe to a temperature condition below the prescribed sooting temperature condition, reheating the treatment atmosphere sample to the desired temperature condition within the sample tube interior for analysis by the external sensor at the distal end by flowing the treatment atmosphere sample, while in the temperature condition below the prescribed sooting temperature condition, from the gas pipe into the sample tube interior through an inlet having an axis that is generally parallel to the sample tube interior axis, which directs the treatment atmosphere sample within the sample tube interior in a flow path that is generally parallel to the sample tube interior axis and extends toward the distal end, increasing the linear flow rate of the treatment atmosphere sample in said flow path compared to its linear flow rate in the gas pipe by constricting the flow of the treatment atmosphere sample along at least a portion of the flow path before reaching the distal end, generating an output signal based upon the analysis by the external sensor of the treatment atmosphere sampled in the distal end of the sample tube interior, and controlling the reacting of the mixture of gases in response to the output signal of the external sensor.

2. A method for producing within a reaction chamber a treatment atmosphere having a carbon potential and subject to formation of carbon when exposed to a prescribed sooting temperature condition, the method comprising the steps of:

heating the reaction chamber to a desired temperature condition above the prescribed sooting temperature condition, reacting a mixture of gases to produce a treatment atmosphere at the desired temperature condition within the heated reaction chamber, locating an external sensor within a sample tube outside the reaction chamber for analyzing an atmosphere sample, the sample tube having an interior and a distal end, the external sensor being located within the sample tube interior near the distal end, heating at least the distal end of the sample tube interior to the desired temperature condition, withdrawing a sample of the treatment atmosphere from the reaction chamber through a gas pipe while cooling the sample from the desired temperature condition within the gas pipe to a temperature condition below the prescribed sooting temperature condition, reheating the treatment atmosphere sample to the desired temperature condition within the sample tube interior for analysis by the external sensor at the distal end by flowing the treatment atmosphere sample, while in the temperature condition below the prescribed sooting temperature condition, from the gas pipe into the sample tube interior through an inlet that directs the treatment atmosphere sample within the sample tube interior in a flow path toward the distal end, increasing the linear flow rate of the treatment atmosphere sample in said flow path compared to its linear flow rate in the gas pipe by directing the treatment atmosphere sample through a constricted passage in the sample tube interior that communicates with the inlet, generating an output signal based upon the analysis by the external sensor of the treatment atmosphere sampled in the distal end of the sample tube interior, and controlling the reacting of the mixture of gases in response to the output signal of the external sensor.

3. A method for producing within a reaction chamber a treatment atmosphere having a carbon potential and subject to formation of carbon when exposed to a prescribed sooting temperature condition, the method comprising the steps of:

heating the reaction chamber to a desired temperature condition above the prescribed sooting temperature condition, reacting a mixture of gases to produce a treatment atmosphere at the desired temperature condition within the heated reaction chamber, locating an external sensor within a sample tube outside the reaction chamber for analyzing an atmosphere sample, the sample tube having an interior that extends along an axis and has a distal end, the external sensor being located within the sample tube interior near the distal end, heating at least the distal end of the sample tube interior to the desired temperature condition, withdrawing a sample of the treatment atmosphere from the reaction chamber through a gas pipe while cooling the sample from the desired temperature condition within the gas pipe to a temperature condition below the prescribed sooting temperature condition, reheating the treatment atmosphere sample to the desired temperature condition within the sample tube interior for analysis by the external sensor at the distal end by flowing the treatment atmosphere sample, while in the temperature condition below the prescribed sooting temperature condition, from the gas pipe into the sample tube interior through an inlet that directs the treatment atmosphere sample in a flow path that is generally parallel to the sample tube interior axis and extends in a direction toward the distal end, the treatment atmosphere sample passing through the prescribed sooting temperature condition while being reheated in the flow path, increasing the linear flow rate of the treatment atmosphere sample in said flow path compared to its linear flow rate in the gas pipe by constricting the flow of the treatment atmosphere sample in the flow path during reheating at least while in the prescribed sooting temperature condition, generating an output signal based upon the analysis by the external sensor of the treatment atmosphere sampled in the distal end of the sample tube interior, and controlling the reacting of the mixture of gases in response to the output signal of the external sensor.

4. A method for producing within a reaction chamber a treatment atmosphere having a carbon potential and subject to formation of carbon when exposed to a prescribed sooting temperature condition, the method comprising the steps of:

heating the reaction chamber to a desired temperature condition above the prescribed sooting temperature condition, reacting a mixture of gases to produce a treatment atmosphere at the desired temperature condition within the heated reaction chamber, locating an external sensor within a sample tube outside the reaction chamber for analyzing an atmosphere sample, the sample tube having an interior and a distal end, the external sensor being located within the sample tube interior near the distal end, heating at least the distal end of the sample tube interior to the desired temperature condition, withdrawing a sample of the treatment atmosphere from the reaction chamber through a gas pipe while cooling the sample within the gas pipe from the desired temperature condition to a temperature condition below the prescribed sooting temperature condition, reheating the treatment atmosphere sample to the desired temperature condition within the sample tube interior for analysis by the external sensor at the distal end by flowing the treatment atmosphere sample, while in the temperature condition below the prescribed sooting temperature condition, from the gas pipe into the sample tube interior through an inlet that directs the treatment atmosphere sample in a flow path toward the distal end, the treatment atmosphere sample passing through the prescribed sooting temperature condition while being reheated in the flow path, increasing the linear flow rate of the treatment atmosphere sample in said flow path compared to its linear flow rate in the gas pipe during reheating at least while in the prescribed sooting temperature condition by directing the treatment atmosphere sample through a constricted passage in the sample tube interior that communicates with the inlet, generating an output signal based upon the analysis by the external sensor of the treatment atmosphere sampled in the distal end of the sample tube interior, and controlling the reacting of the mixture of gases in response to the output signal of the external sensor.

5. A method according to claim 1 or 2 or 3 or 4 wherein the increased linear flow rate is between about 300 feet per minute and about 4000 feet per minute.

6. A method according to claim 1 or 2 or 3 or 4 wherein the increased linear flow rate is about 1500 feet per minute.

7. A method according to claim 1 or 2 or 3 or 4 and further including the step of decreasing the linear flow rate of the treatment atmosphere sample within the sample tube interior during reheating near the distal end for analysis by the external sensor.

8. A method according to claim 7 wherein the decreased linear flow rate is between about 1 to 10 feet per minute.

9. A method according to claim 7 wherein the decreased linear flow rate is about 4 feet per minute.

10. A method according to claim 1 or 2 or 3 or 4 and further including the step of venting the treatment atmosphere sample from the sample tube interior after reheating.

\* \* \* \* \*